(12) United States Patent
Thomason et al.

(10) Patent No.: US 8,545,461 B2
(45) Date of Patent: Oct. 1, 2013

(54) AUTOMATIC BODY SPRAY SYSTEM EXCESS LIQUID REMOVAL

(75) Inventors: Scott Thomason, Macedonia, OH (US); Nicholas J Mastandrea, Chardon, OH (US)

(73) Assignee: Sunless, Inc., Macedonia, OH (US)

( * ) Notice: Subject to any disclaimer, the term of this patent is extended or adjusted under 35 U.S.C. 154(b) by 179 days.

(21) Appl. No.: 12/837,134

(22) Filed: Jul. 15, 2010

(65) Prior Publication Data

US 2010/0291847 A1 Nov. 18, 2010

Related U.S. Application Data

(63) Continuation of application No. 12/546,056, filed on Aug. 24, 2009, now Pat. No. 8,201,288, and a continuation of application No. 11/650,323, filed on Jan. 5, 2007, now abandoned.

(60) Provisional application No. 60/756,304, filed on Jan. 5, 2006.

(51) Int. Cl.
*A61M 35/00* (2006.01)
*B05B 15/12* (2006.01)
*A47K 3/28* (2006.01)

(52) U.S. Cl.
USPC .................................. 604/289; 454/50; 4/600

(58) Field of Classification Search
USPC ........................................ 4/600, 615; 454/49
See application file for complete search history.

(56) References Cited

U.S. PATENT DOCUMENTS

| 1,982,509 | A | 11/1934 | Frank |
| 4,142,257 | A | 3/1979 | Mace |
| 4,282,612 | A | 8/1981 | King |
| 4,798,341 | A | 1/1989 | Gimple |
| 4,964,399 | A | 10/1990 | Faimali |

(Continued)

FOREIGN PATENT DOCUMENTS

| DE | 20316174 | 4/2004 |
| ES | 2231034 | 1/2005 |

(Continued)

OTHER PUBLICATIONS

Thomason, Scott; Final Office Action in U.S. Appl. No. 12/623,687, Feb. 22, 2011.

(Continued)

*Primary Examiner* — Susan Su
(74) *Attorney, Agent, or Firm* — Benesch Friedlander Coplan & Aronoff, LLP

(57) ABSTRACT

An embodiment of an apparatus for extracting excess liquid in a human body spray system includes a spray booth defining a booth volume. The spray booth includes a base configured to support the human body and a column having walls extending vertically from the base and at least one vent opening disposed on a bottom half portion of the column on at least one of the walls. The walls form a hollow interior of the column. The apparatus for extracting excess liquid in a human body spray system further includes an extraction fan disposed within the hollow interior adjacent to a top half portion of the column and configured to create a low pressure volume within the hollow interior and draw air flow and at least some of the excess mist from the booth volume through the at least one vent opening.

10 Claims, 18 Drawing Sheets

(56) References Cited

U.S. PATENT DOCUMENTS

| | | | |
|---|---|---|---|
| 4,967,956 | A | 11/1990 | Mansfield |
| 4,991,776 | A | 2/1991 | Smith |
| 5,064,119 | A | 11/1991 | Mellette |
| 5,074,467 | A | 12/1991 | Geberth |
| 5,496,214 | A * | 3/1996 | Marcreigns ............... 454/341 |
| 5,853,215 | A | 12/1998 | Lowery |
| 5,922,333 | A | 7/1999 | Laughlin |
| 5,927,565 | A | 7/1999 | Paczonay |
| 6,085,997 | A | 7/2000 | Mills et al. |
| 6,199,557 | B1 | 3/2001 | Laughlin |
| 6,251,374 | B1 | 6/2001 | Laughlin |
| 6,298,862 | B1 | 10/2001 | Laughlin |
| 6,302,122 | B1 | 10/2001 | Parker |
| 6,305,384 | B2 | 10/2001 | Laughlin |
| 6,387,081 | B1 | 5/2002 | Cooper |
| 6,412,707 | B1 | 7/2002 | Wirz |
| 6,416,747 | B1 | 7/2002 | Laughlin |
| 6,431,180 | B2 | 8/2002 | Laughlin |
| 6,439,243 | B2 | 8/2002 | Laughlin |
| 6,443,164 | B1 | 9/2002 | Parker |
| 6,446,635 | B2 | 9/2002 | Laughlin |
| 6,468,508 | B1 | 10/2002 | Laughlin |
| 6,474,343 | B2 | 11/2002 | Laughlin |
| 6,554,208 | B1 * | 4/2003 | Venuto, Sr. ............... 239/207 |
| 6,656,455 | B2 | 12/2003 | Laughlin |
| 6,782,893 | B2 | 8/2004 | Laughlin |
| 6,799,580 | B2 | 10/2004 | Laughlin |
| 6,881,417 | B1 | 4/2005 | Laughlin |
| 6,886,572 | B2 | 5/2005 | Laughlin |
| 6,899,108 | B2 | 5/2005 | Laughlin |
| 6,918,897 | B2 | 7/2005 | Severino |
| 7,004,407 | B2 | 2/2006 | Cooper |
| 7,041,089 | B2 | 5/2006 | Laughlin |
| 7,082,948 | B2 | 8/2006 | Laughlin |
| 7,297,211 | B2 | 11/2007 | Cooper |
| 7,387,684 | B2 | 6/2008 | Cooper |
| 7,462,242 | B2 | 12/2008 | Cooper |
| 7,569,037 | B1 | 8/2009 | Spivak |
| 7,699,882 | B2 | 4/2010 | Stamper |
| 7,886,684 | B2 | 2/2011 | Cooper |
| 7,913,918 | B2 | 3/2011 | Zellner |
| 7,992,517 | B2 | 8/2011 | Cooper |
| 8,069,812 | B2 | 12/2011 | Lotterhos |
| 2002/0000237 | A1 | 1/2002 | Laughlin |
| 2002/0096186 | A1 | 7/2002 | Von Halem |
| 2002/0112738 | A1 | 8/2002 | Parker |
| 2003/0029488 | A1 | 2/2003 | Baird |
| 2003/0094509 | A1 | 5/2003 | Venuto, Sr. |
| 2003/0127542 | A1 | 7/2003 | Cooper |
| 2004/0069321 | A1 | 4/2004 | Maleville |
| 2004/0073186 | A1 | 4/2004 | Cameron |
| 2004/0089315 | A1 | 5/2004 | Laughlin |
| 2004/0116880 | A1 | 6/2004 | Venuto, Sr. |
| 2004/0232257 | A1 | 11/2004 | Venuto, Sr. |
| 2004/0241106 | A1 | 12/2004 | Venuto, Sr. |
| 2004/0251272 | A1 | 12/2004 | Hunter |
| 2005/0022807 | A1 | 2/2005 | Laughlin |
| 2005/0193945 | A1 | 9/2005 | Coffield |
| 2005/0252445 | A1 | 11/2005 | Laughlin |
| 2005/0279865 | A1 | 12/2005 | Thomason |
| 2006/0005850 | A1 | 1/2006 | Laughlin |
| 2006/0032439 | A1 | 2/2006 | Laughlin |
| 2006/0118039 | A1 | 6/2006 | Cooper |
| 2006/0124779 | A1 | 6/2006 | Cooper |
| 2006/0163382 | A1 | 7/2006 | Spivak |
| 2006/0180682 | A1 | 8/2006 | Burato et al. |
| 2006/0275555 | A1 | 12/2006 | Colizza |
| 2007/0107121 | A1 | 5/2007 | Smith |
| 2007/0125798 | A1 | 6/2007 | McGuire |
| 2007/0169261 | A1 | 7/2007 | Smith |
| 2007/0186340 | A1 | 8/2007 | Gay |
| 2007/0197982 | A1 | 8/2007 | Thomason |
| 2008/0072376 | A1 * | 3/2008 | Guerin et al. ............... 4/597 |
| 2009/0031949 | A1 * | 2/2009 | Nagase et al. ............... 118/326 |
| 2009/0157015 | A1 | 6/2009 | Lotterhos |
| 2009/0211592 | A1 | 8/2009 | Waters |
| 2009/0314857 | A1 | 12/2009 | Thomason |
| 2010/0001097 | A1 | 1/2010 | Spivak |
| 2010/0122745 | A1 | 5/2010 | Thomason |
| 2010/0129557 | A1 | 5/2010 | Thomason |
| 2010/0145529 | A1 | 6/2010 | Thomason |
| 2010/0266776 | A1 | 10/2010 | Cooper |
| 2010/0291847 | A1 | 11/2010 | Thomason |

FOREIGN PATENT DOCUMENTS

| | | |
|---|---|---|
| WO | 03013648 | 2/2003 |
| WO | 2004/006932 | 1/2004 |
| WO | 2004/069321 | 8/2004 |
| WO | 2005/094754 | 10/2005 |
| WO | 2006/104705 | 10/2006 |

OTHER PUBLICATIONS

Thomason, Scott; Office Action in U.S. Appl. No. 12/623,687, Sep. 1, 2010.

Office Action in corresponding U.S. Appl. No. 12/623,687, filed Nov. 23, 2009; dated Feb. 23, 2012.

Office Action in corresponding U.S. Appl. No. 12/624,149, filed Nov. 23, 2009; dated Aug. 7, 2012.

Office Action in corresponding U.S. Appl. No. 12/624,083, filed Nov. 23, 2009; dated Jun. 12, 2012.

Fu, Jennifer M. et al.; "Sunless Tanning"; Journal of the American Academy of Dermatology, vol. 50, Issue 5, May 2004, pp. 706-713.

Webpages associated with www.mist-on.com, published at least as early as Apr. 2004 by Mist-On Systems, Inc., accessed via web archive on Jun. 11, 2013.

Webpages associated with www.mystictan.com, published at least as early as Dec. 2005 by Mystic Tan, Inc., accessed via web archive on Jun. 11, 2013.

Webpages associated with www.magictancorp.com, published at least as early as Jun. 2004, by MagicTan, Inc., accessed via web archive on Jun. 11, 2013.

Webpages associated with www.hollywoodtan.com, published at least as early as Feb. 2005, by Hollywood Tan, Inc., accessed via web archive on Jun. 11, 2013.

Fresh'n Up Model 500003 Parts Guide, published on Aug. 15, 2005 by Industrial Vacuum Systems.

Quick Track Linear Motion System Catalog, published in 2005 by BishopWisecarver.

LoPro Linear Motion System Catalog, published in 2002 by BishopWisecarver.

*Sunless, Inc.* v. *Heartland Tanning, Inc.*, USDC Eastern District of Texas, Tyler Division, Case No. 6:12-cv-00665-LED; Heartland Tanning, Inc.'s Answer and Amended Counterclaims, Redacted for IDS, filed Jun. 17, 2013.

Marine Plumbing Catalog, published Jan. 2005 by John Guest USA, Inc.

Statement of Related Litigation, U.S. Appl. No. 12/837,134, filed on Jul. 3, 2013.

Webpages associated with www.mystictan.com, "The Most Beautiful Tan Under the Sun . . ." published at least as early as Dec. 2005 by Mystic Tan, Inc., accessed via web archive on Jun. 11, 2013.

Webpages associated with www.magictancorp.com, "Serious Tan, Seriously Fast, UV-Free", published at least as early as Jun. 2004, by MagicTan, Inc., accessed via web archive on Jun. 11, 2013.

*Sunless, Inc.* v. *Heartland Tanning, Inc.*, USDC Eastern District of Texas, Tyler Division, Case No. 6:12-cv-00665-LED; Heartland's Initial Invalidity Contentions, filed Jun. 17, 2013.

*Sunless, Inc.* v. *Heartland Tanning, Inc.*, USDC Eastern District of Texas, Tyler Division, Case No. 6:12-cv-00665-LED; Heartland's Appendices A-1 to A-12.

* cited by examiner

AUTOMATIC BODY SPRAY SYSTEM EXCESS LIQUID REMOVAL

CROSS-REFERENCE TO RELATED APPLICATIONS

This application is a continuation of U.S. Non-Provisional application Ser. No. 12/546,056 filed on Aug. 24, 2009, which is a continuation of U.S. Non-Provisional application Ser. No. 11/650,323 filed on Jan. 5, 2007, which claims priority from U.S. Provisional Application Ser. No. 60/756,304 filed on Jan. 5, 2006, the disclosures of which are hereby incorporated by reference in their entirety.

BACKGROUND

There are many lotions and products applied to the human body for cosmetic purposes. These products include moisturizers, sunscreens, anti-aging treatments, UV tanning accelerators, sunless tanning products and much more. There are numerous forms of artificial tanning products currently available, including lotions, creams, gels, oils, and sprays. These products are typically mixtures of a chemically-active skin colorant or a bronzer, in combination with moisturizers, preservatives, anti-microbials, thickeners, solvents, emulsifiers, fragrances, surfactants, stabilizers, sunscreens, pH adjusters, anti-caking agents, and additional ingredients to alter the color reaction.

There exist many automated systems for applying artificial tanning products and often include a closed booth provided with a spraying system. The spraying systems typically use high pressure compressed air nozzles, along with a fluid supplied to the nozzle to create an atomized spray directed towards the body. Currently, these booths are mostly closed, are limited to applying only one product per session, and create a foggy closed environment for the user.

BRIEF DESCRIPTION OF THE DRAWINGS

In the accompanying drawings and descriptions that follow, like parts are indicated throughout the drawings and description with the same reference numerals, respectively. One of ordinary skill in the art will appreciate that one element can be designed as multiple elements or that multiple elements can be designed as one element. An element shown as an internal component of another element can be implemented as an external component and vice versa. The figures are not drawn to scale and the proportions of certain parts have been exaggerated for convenience of illustration.

DETAILED DESCRIPTION

Figure 1:
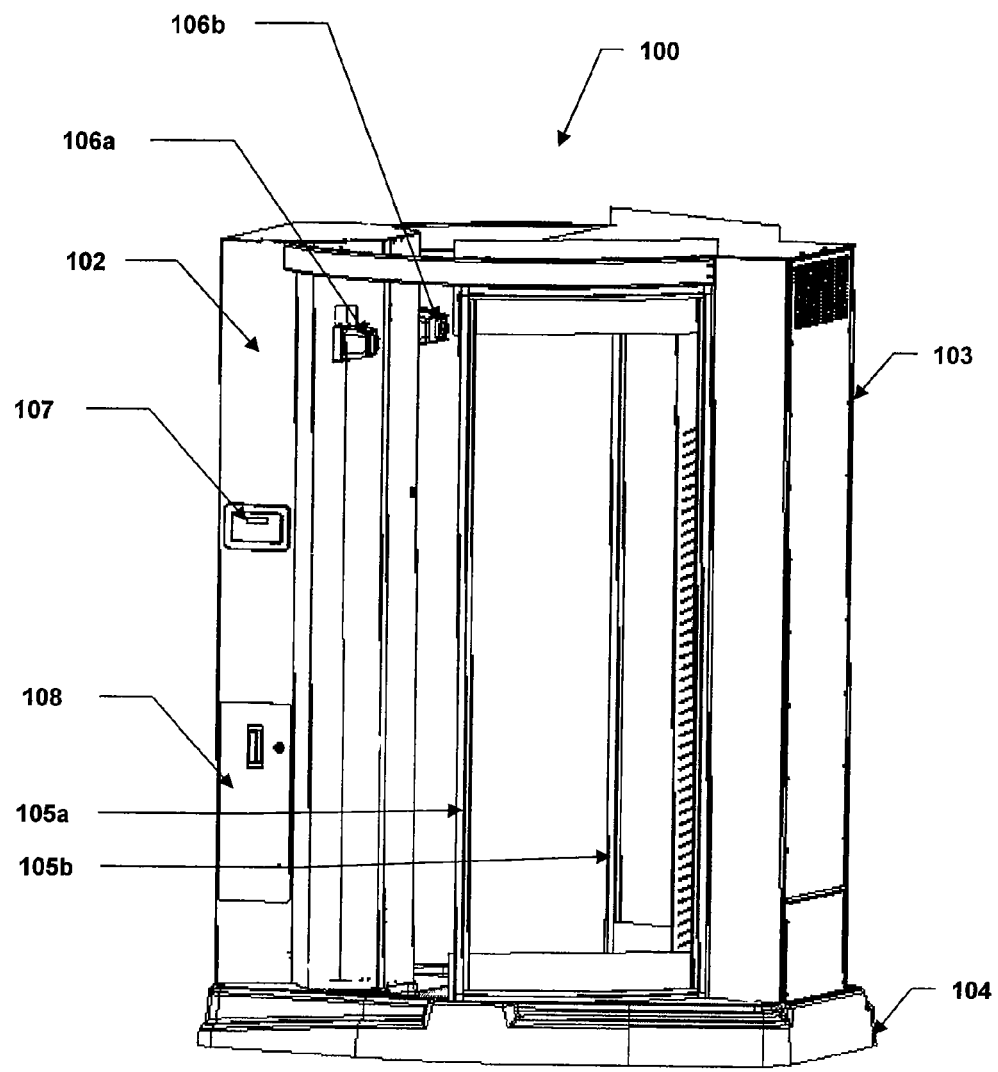
FIG. 1 is a front-right perspective view of one embodiment of an automatic body spray system 100.
Figure 2:
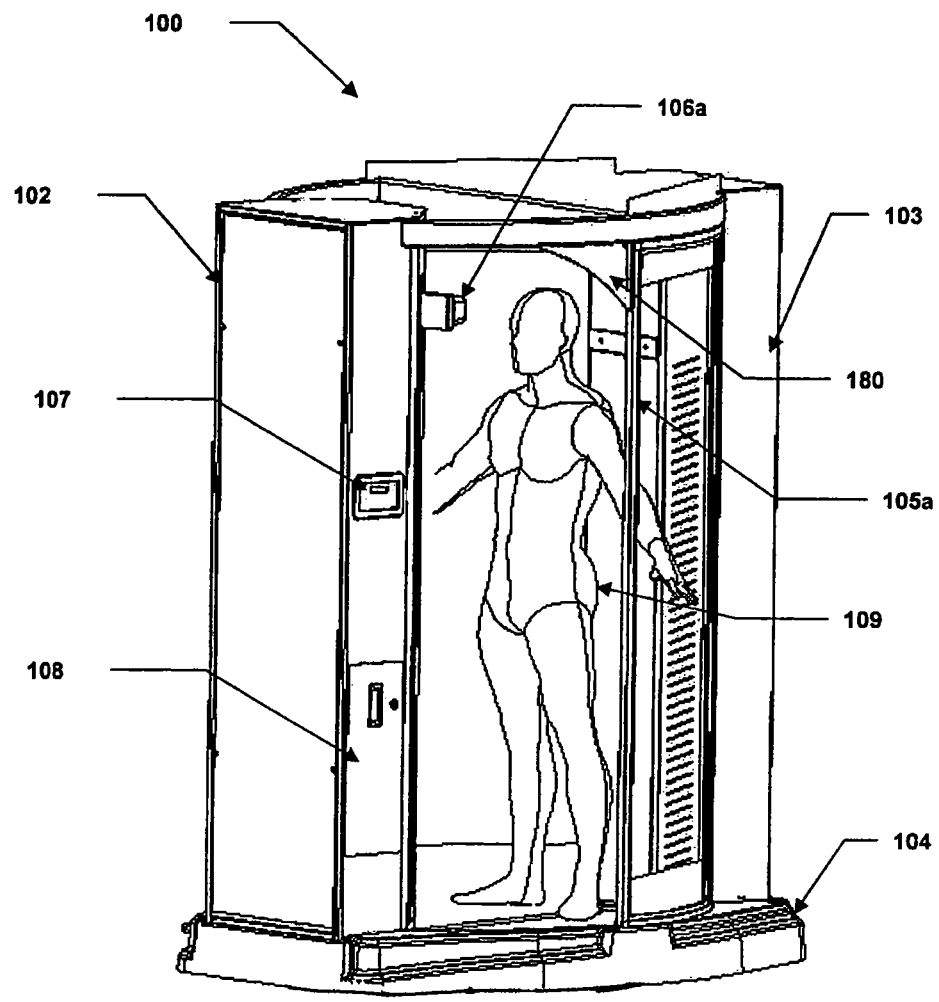
FIG. 2 is a front-left perspective view of the automatic body spray system 100.

FIGS. 1 and 2 illustrate left and right perspective views, respectively, of on embodiment of an automatic body spray system 100. The system 100 includes a base 104 configured to support a human body 109. Extending vertically from the perimeter of the base 104 are a spray column 102, a mist extraction column 103, and partial side walls 105a, 105b, which together defined a spray booth to house the user therein. These partial sidewalls 105a,b contact the spray column 103 and continue in a curved pattern toward the spray column 102 (see also FIG. 15). The partial sidewalls 105a,b also seat against the base 104 at the bottom of the system 100. The partial sidewalls 105a,b stop short of the spray column 103 to allow for user access into the system 100. The partial sidewalls 105a,b can be of any shape or size and can be modified to provide the desired amount of mist containment. A partial top 180 can also be provided to keep any excess mist from escaping out the top of the system 100. In an alternative embodiment, the system 100 can include full-size sidewalls, instead of partial walls.

In a preferred embodiment, the system 100 can be employed to apply sunless tanning solutions as well as other solutions onto a human body 109. Exemplary sunless-tanning solutions include one or more colorants, such as dihydroxyacetone, crotonaldehyde, pyruvaldehyde, glycolaldehyde, glutaraldehyde, otho-phthaldehyde, sorbose, fructose, erythrulose, methylvinylketone, food coloring, or any other available colorant. The sunless tanning solutions can additionally or alternatively include one or more bronzers, such as lawsone, juglone, or any other available bronzer. It will be appreciated that the sunless-tanning solutions can include additional ingredients, such as moisturizers and scents, to make the solution more appealing to a user.

While the system 100 can be employed as a sunless tanning spray system, it can also be employed to spray other fluids onto the human body. For example, the system 100 can be configured to spray sunscreens, suntan lotions, moisturizing lotions, sunless tanning pre-spray treatments, tanning accelerators, sunburn treatments, insect repellants, skin toners, skin bleaches, skin lighteners, anti-microbial compositions, exfoliants, nutriments or vitamins, massage aides, muscle relaxants, skin treatment agents, burn treatment agents, decontamination agents, cosmetics, or wrinkle treatments or removers, or any other solution or lotion desired to be applied to the human body.

Figure 3:
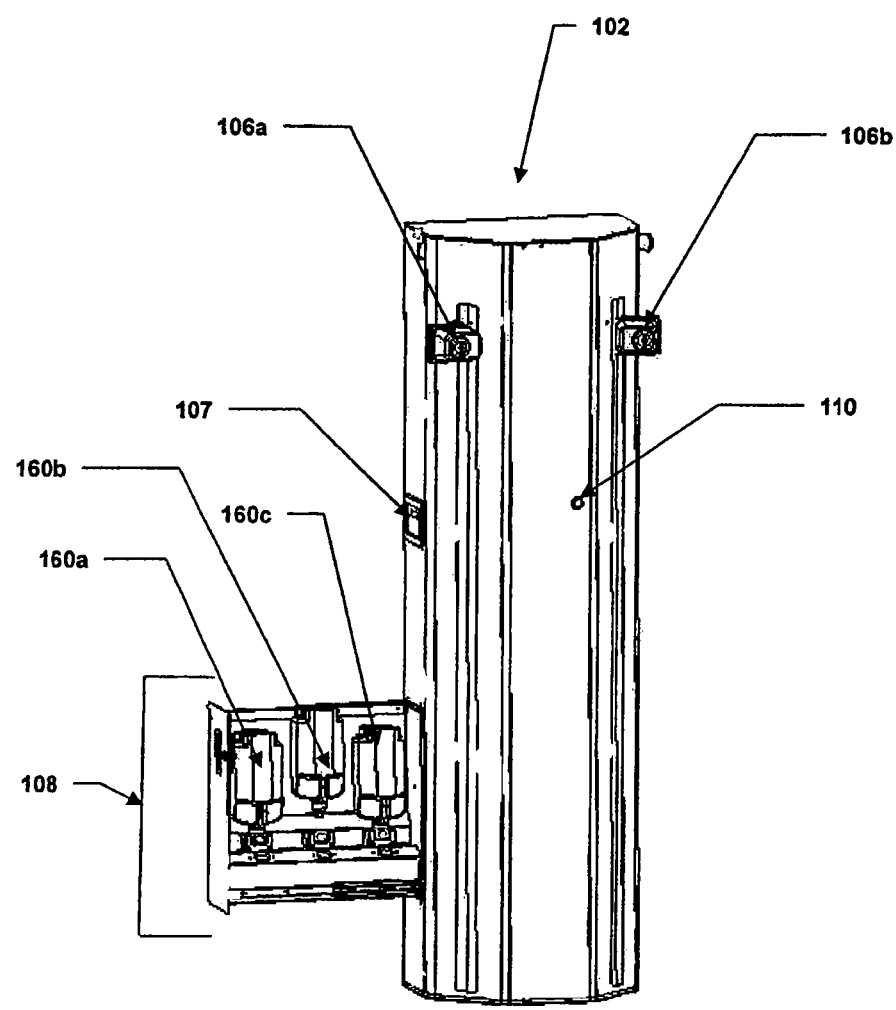
FIG. 3 is a perspective view of one embodiment of a spray column 102 showing one embodiment of a slide out drawer 108 holding multiple solution containers 160a-c.

As shown in FIG. 3, the spray column 102 includes two high volume, low pressure (HVLP) atomization nozzles 106a,b fluidly connected to an HVLP turbine (not shown) with an air supply hose and also fluidly connected to at least one fluid container 160. With the assistance of the HVLP turbine, the HVLP nozzles 106a,b are configured to eject an atomized mist of fluid. In alternative embodiments (not shown), the spray column 102 may include one HVLP nozzle or more than two HVLP nozzles. In another embodiment (not shown), a high pressure fluid pump may be employed, instead of the HVLP turbine.

Each HVLP nozzle 106a,b is coupled to a linear slide (not shown) that is configured to move the HVLP nozzles 106a,b up and down vertically, thereby adjusting the vertical of the HVLP nozzle 106a,b. In this configuration, the HVLP nozzles 106a,b are moveably mounted to the spray column 102, such that the spray pattern of the HVLP nozzles 106a,b is sufficient to completely coat the human body 109 with a desired fluid, solution, or lotion.

Figure 4:
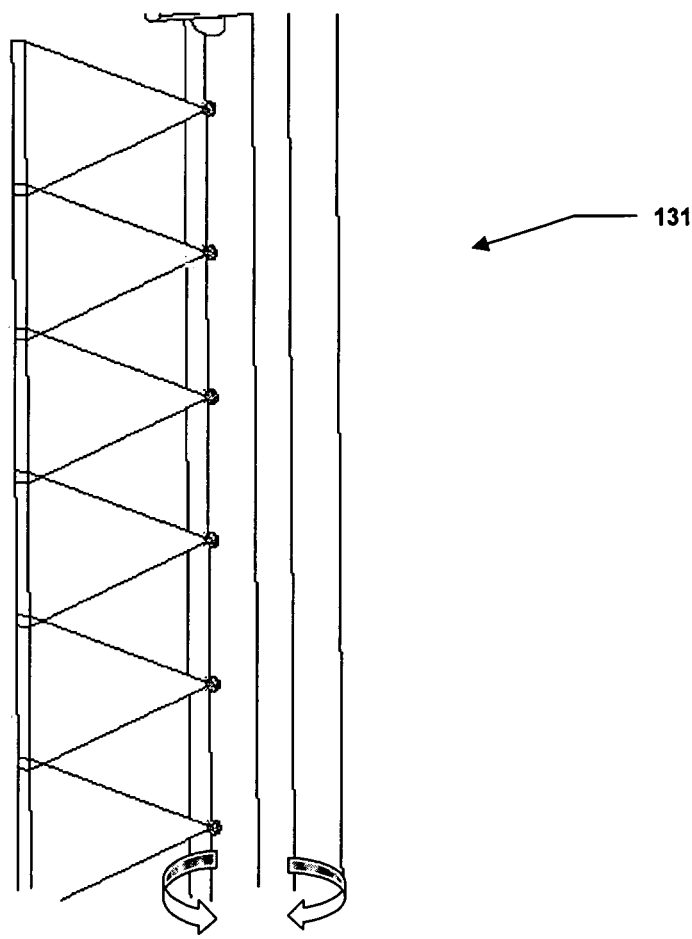
FIG. 4 is a perspective view of one embodiment of a rotating nozzle column 131.

In an alternative embodiment as shown in FIG. 4, a vertically standing column 131 that rotates back and forth about its vertical axis can be employed. One or more HVLP nozzles 106 can be mounted to the rotating column 131 and be connected to an HVLP turbine with an air supply hose and also fluidly connected to at least one fluid reservoir or container 160. This column can be automatically rotated back and forth to automatically coat the human body.

With reference back to FIG. 3, the system 100 includes three fluid containers 160ac contained in the drawer 108. In alternative embodiments, the system 100 can include two or less containers or more than three containers provided in the drawer 108.

As shown in FIG. 3, a start button 110 and an LCD user interface panel 107 are also provided. The start button 110 is used to initiate a session. The LCD user interface is used to set up a session and also to perform other functions including, but not limited to, defining the system parameters, turning on a wash down function, turning on a light, and viewing session counts.

Figure 5:
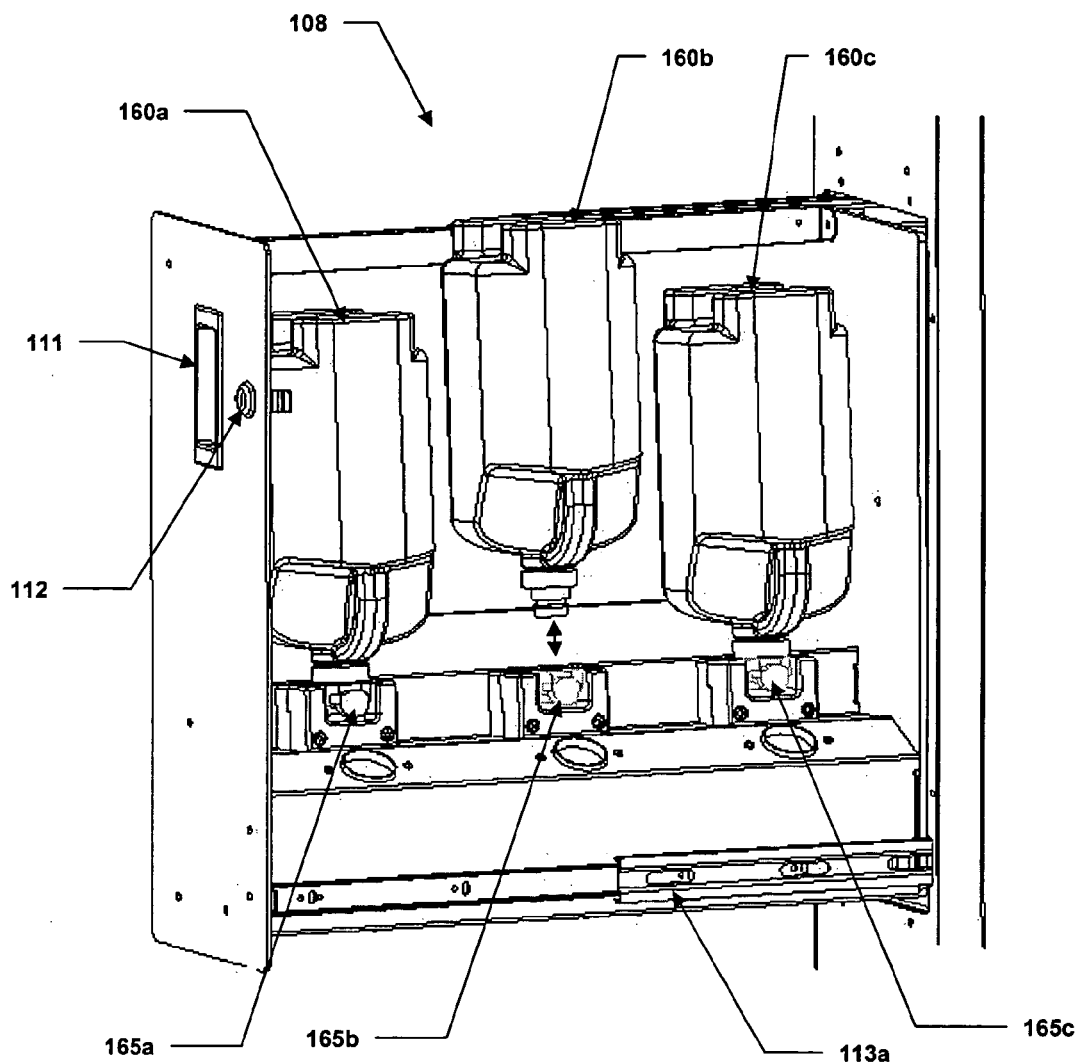
FIG. 5 is a detailed perspective view of the slide out drawer 108 holding multiple solution containers 160a,b,c for use in the spray system 100.

FIG. 5 illustrates a perspective view of the fluid container drawer 108 with the drawer 108 opened to expose the fluid containers 160a,b,c. The drawer 108 provides for a simple method of accessing the containers 160. The drawer 108 includes a pull handle 111 and a key lock 112 for security purposes. In this embodiment, the drawer 108 is attached to the spray column 102 with two slide rails 113a,b. The drawer 108 can also be attached to the spray column using a rotating mount or any other type of mount.

As discussed in more detail above, the fluid containers 160a-c can hold sunless tanning solutions or other types of fluids. In one embodiment, each fluid container 160a-c can hold a different sunless-tanning solution. The different solutions can have different chemical compositions which affect the hue of the resulting tan. Alternatively, one fluid container (e.g., the first fluid container 160a) can contain water or another dilution agent to dilute a solution contained in the second solution container (e.g., the second fluid container 160b). The contents of the different fluid containers can be mixed in various combinations to provide a range of shades, thereby allowing the user to select a preferred tanning shade. Also, the fluid containers can hold other types of solutions to be applied to the human body. One control method for applying the solutions can be to apply a first atomized solution, dry the body with air only coming from the HVLP nozzles, apply a second atomized solution, dry the body with air only coming from the HVLP nozzles, apply a third atomized solution and then dry the body with air only coming from the HVLP nozzles.

Figure 6:
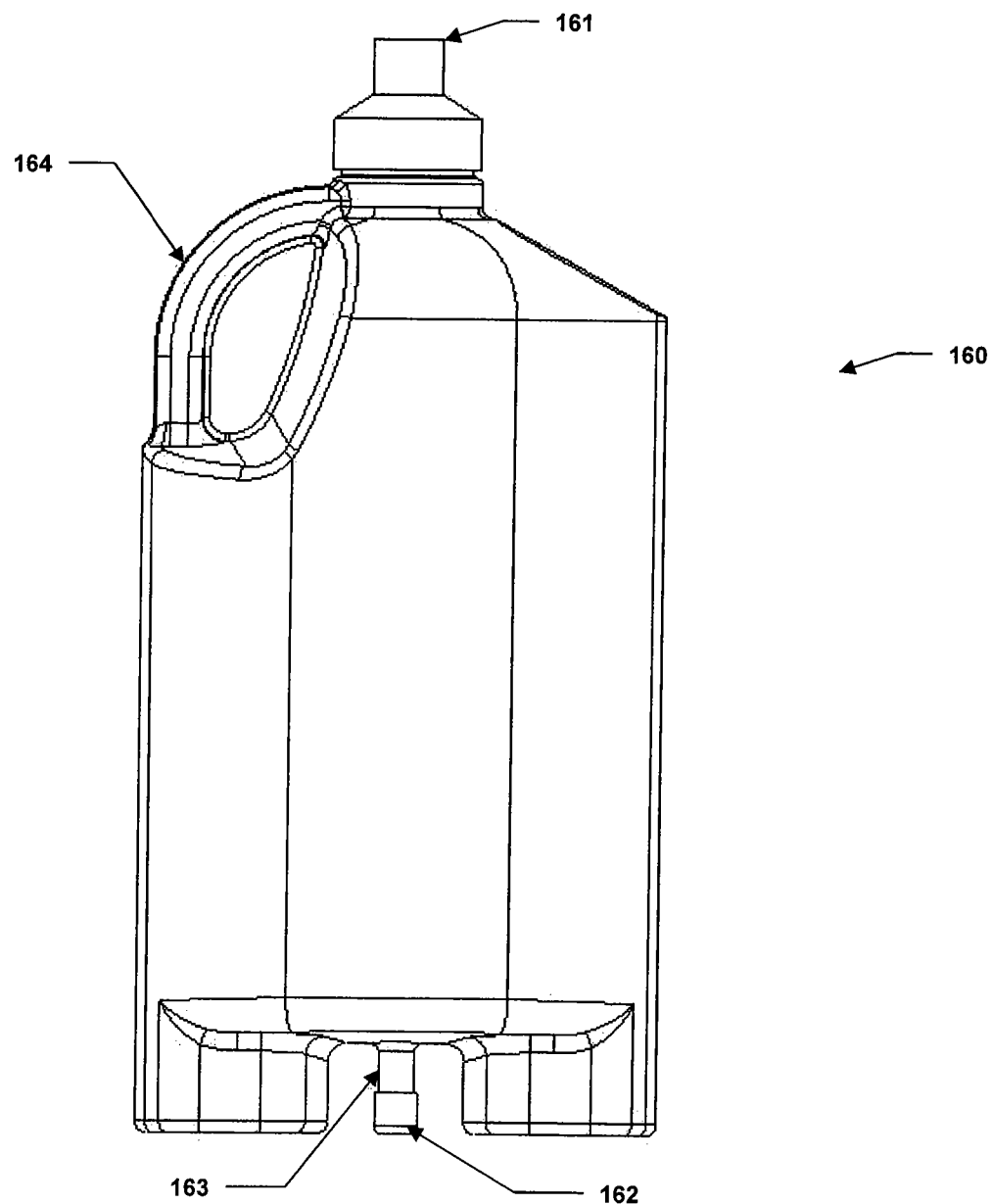
FIG. 6 is a side view of one embodiment of a fluid container 160.

FIG. 6 illustrates a side view of one embodiment of a fluid container 160. In this embodiment, the fluid container 160 includes a handle 164, a male quick disconnect valve 161 at an opening located at one end portion of the fluid container 160, and a vent 162 provided at the other end portion of the fluid container 160. The fluid container 160 can also include a check valve 163 to ensure that fluid flows in only one direction such that, when the fluid container 160 is empty, the check valve 163 will prevent any residual solution from leaking out when the fluid container 160 is removed. It will be appreciated that the fluid container 160 can be configured differently in shape and size from the one illustrated in FIG. 6. Also, it will be appreciated that different fittings such as interchange couplings, poppet couplings, or threaded couplings, can be used to dispense solution from the fluid container 160.

In one embodiment, the fluid containers 160a-c are removable. Alternatively, the spray column 102 can house fixed fluid containers that can be filled with solution while still in spray column 102 when the solution level falls below a predetermined threshold.

As shown in FIG. 4, each fluid container 160a-c is inverted such that the male quick disconnect valve 161 mates with a female quick disconnect fitting 165a-c disposed in the drawer 108. When a new fluid container 160 is added to the system 100, the male quick disconnect valve 161 of the fluid container 160 is snapped into the female quick disconnect fitting 165a-c in the drawer 108. The vent 162 on the fluid container 160 can then be opened to equalize the air pressure inside the fluid container 160, allowing fluid to flow freely.

Figure 7:
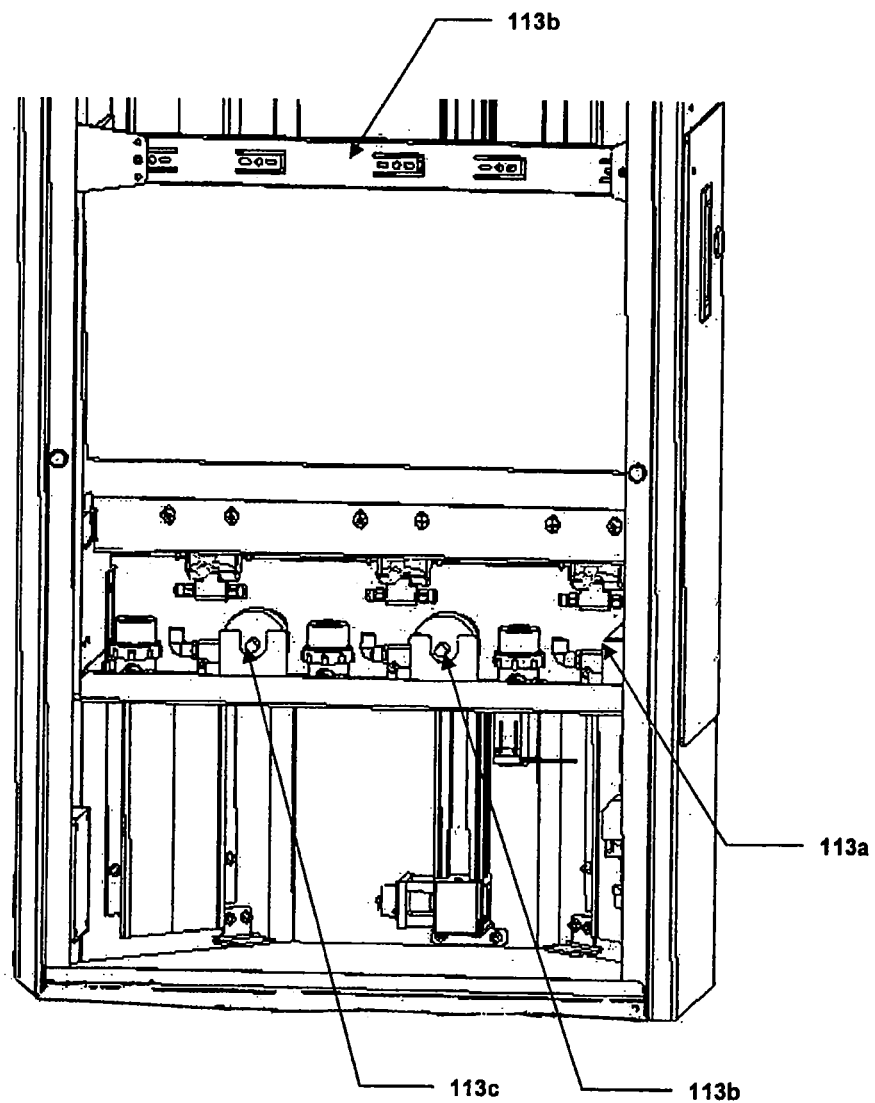
FIG. 7 is a perspective view of the backside of the slide out drawer 108 holding multiple solution containers 160a,b,c showing fluid pumps 113a-c.

FIG. 7 is a perspective view of the inside of the drawer 108 containing three fluid pumps 113a-c positioned below the female quick disconnect fittings 165a-c. The first pump 113a is configured to pump the solution held in the first fluid container 160a along a fluid flow path F1 through the hose assembly 116 to the HVLP nozzle assemblies 106a,b. The second pump 113b is configured to pump the solution held in the second fluid container 160b along a fluid flow path F2 through the hose assembly 116 to the HVLP nozzle assemblies 106a,b. the third pump 113c is configured to pump the solution held in the second fluid container 160c along a fluid flow path F3 through the hose assembly 116 to the HVLP nozzle assemblies 106a,b. In one embodiment, the pumps 130a,b,c are positive displacement pumps. Any other type of fluid pump may suffice. It will be appreciated, however, that one or more of the pumps 113a,b,c can be positioned anywhere in the drawer 108.

Figure 8:
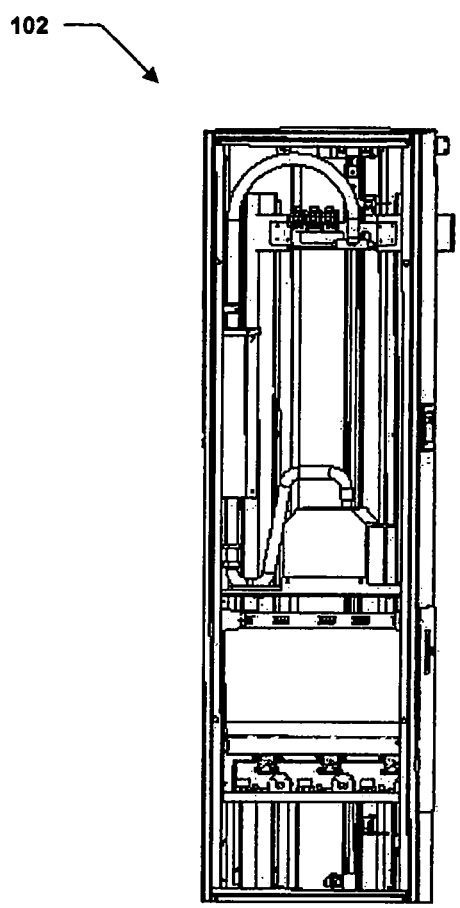
FIG. 8 is a perspective view of one embodiment of the spray column 102 with the back cover removed to expose the internal components.
Figure 9:
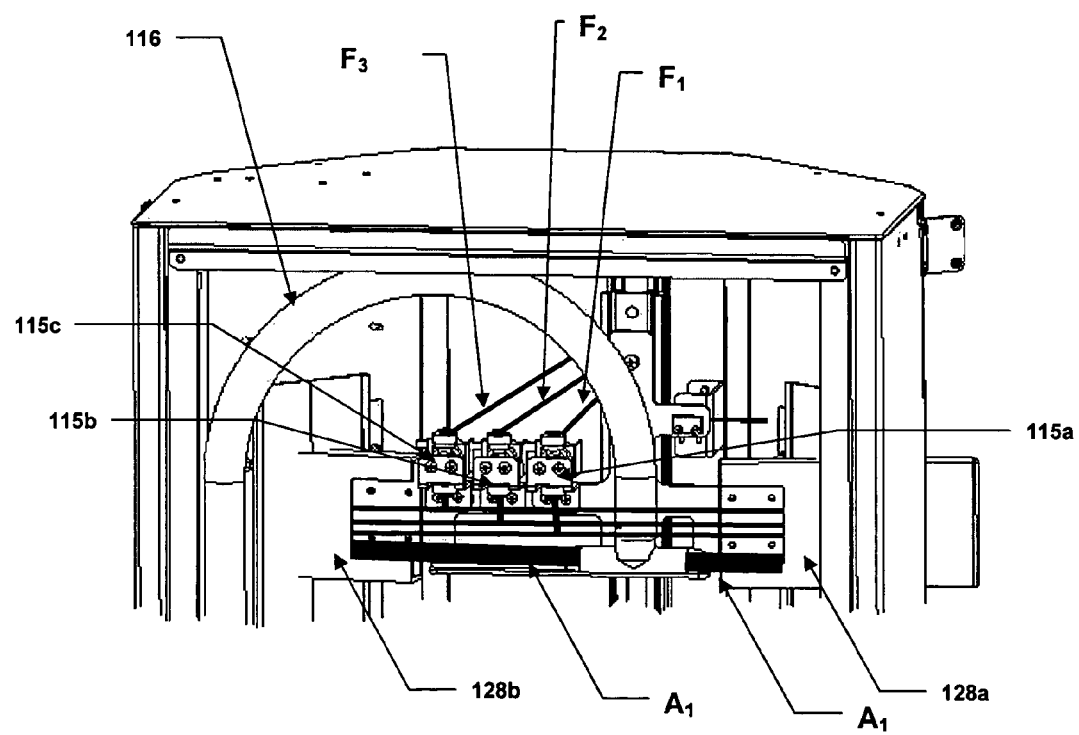
FIG. 9 is a perspective view of the nozzle arms 128a,b and fluid solenoid valves 115a,b,c located in the spray column 102.

FIG. 8 illustrates a simplified perspective view of the interior of the spray column 102. FIG. 9 is a close up view of FIG. 8 showing the HVLP nozzle mounting arms 128a,b in one embodiment of the system 100. The nozzle mounting arms 128a,b also hold fluid solenoid valves 115a-c. These solenoid valves 115a-c turn on or off the fluid flow through fluid paths F1, F2, and F3 between fluid pumps 113a-c and the HVLP nozzle assemblies 106a,b. The solenoid valves are controlled by the controller 122. The valves 115a-c can also be any type of suitable control valve. The hose assembly 116 holds the fluid paths F1, F2, and F3 as well as the air path A1. The three fluid paths F1, F2, F3 route to each solenoid valves 115a-c, respectively, and than to each nozzle assembly 106a,b. The air path A1 routes to each nozzle assembly 106a,b from the HVLP turbine 118 and through hose assembly 116.

Figure 10:
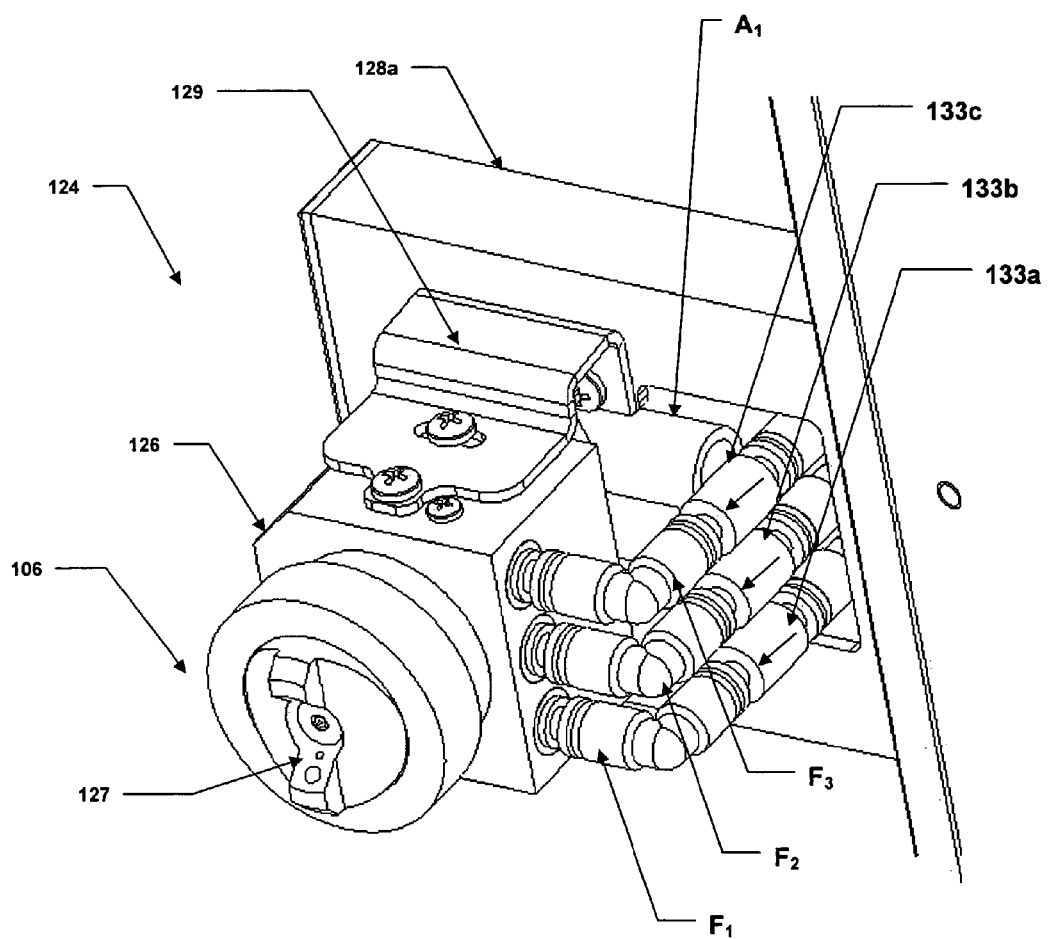
FIG. 10 is a detailed perspective view of one embodiment of an HVLP nozzle assembly 124.

FIG. 10 shows a detailed perspective view of an HVLP nozzle 106 and mounting arm assembly 124. The top of nozzle body 126 mounts to the bottom side of the nozzle mounting bracket 129. The nozzle mounting bracket 129 mounts to the moveable nozzle arm 128a or 128b. The HVLP air supply line A1 enters the nozzle body 126 from the backside and the three fluid lines F1, F2, F3 all enter the nozzle body 126 from one of the other sides. The fluid paths for F1, F2, F3 all merge toward the center of the nozzle body 126 internally and exit at nozzle tip 127. The HVLP air supply from the air path A1 also exits the nozzle body 126 at the nozzle tip 127. In this embodiment, the HVLP air and the fluid are externally atomized at the nozzle tip 127. It can be appreciated that any number of fluid paths may enter the nozzle body 126. Also shown in FIG. 10 are check valves 133a-c. The nozzle body 126 with multiple inlet ports and the check valves 133a-c allow multiple solutions to enter the nozzle body 126 and eliminate any cross contamination of different fluids.

Figure 11:
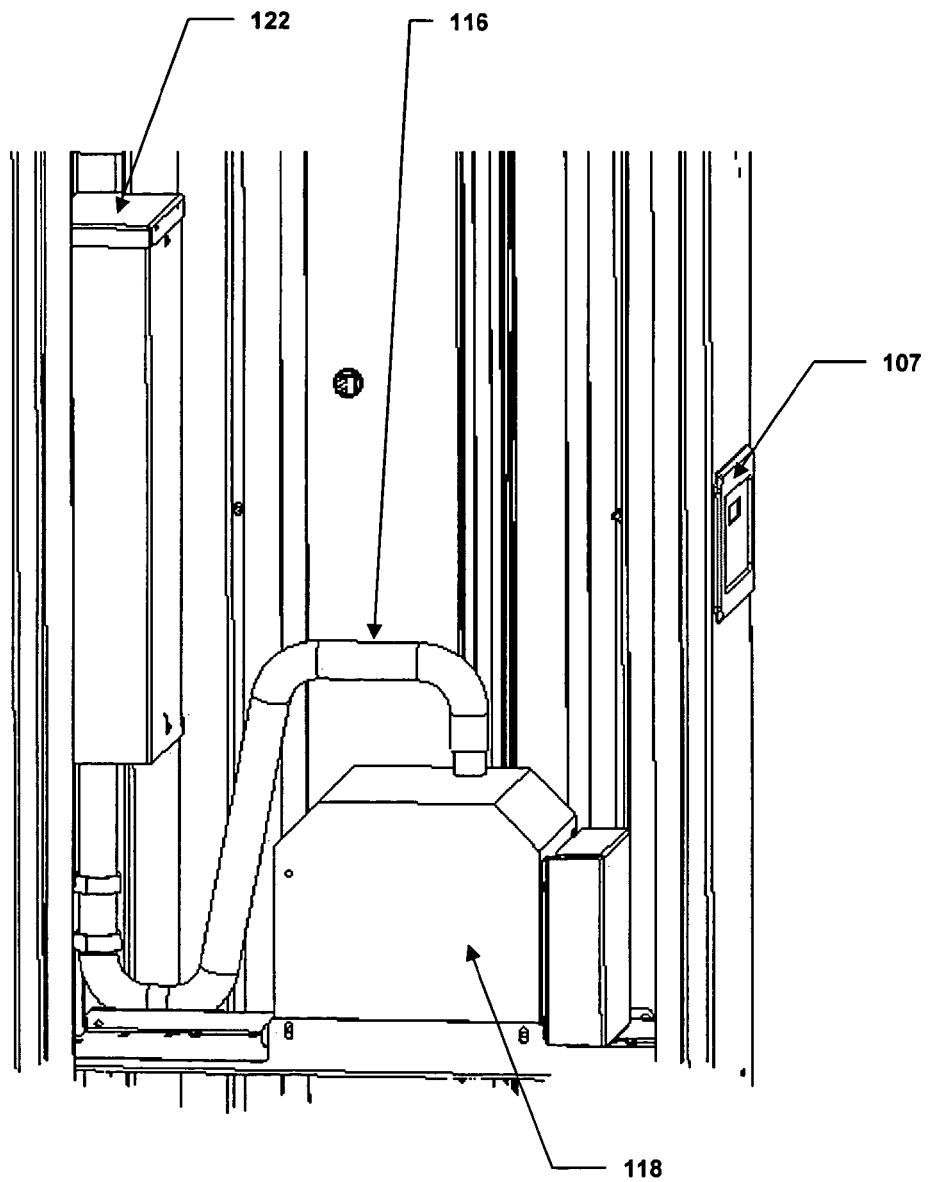
FIG. 11 is a perspective view of the HVLP turbine 118, CPU controller 122, and user interface 117 located in the spray column 102 of the spray system 100.

FIG. 11 is a close up view of FIG. 8 showing the HVLP fan 118 mounted inside the spray column 102. The hose assembly 116 carries the air path A1 from the HVLP fan 118 to the nozzle assemblies 106a,b. The HVLP fan 118 can be controlled on or off by use of a relay or other type of electronic switch. The relay or switch is controlled by the main controller 122. This HVLP fan 118 acts as the air source to atomize any desired solution or fluid. Another embodiment is to have a heating source that the HVLP air passes through to provide a warmer spray and dry session to the user. This heating source can be controlled by the controller 122.

In the illustrated embodiment, the controller 122 is configured to control the operation of the system 100. Specifically, the controller 122 is configured to operate the HVLP nozzles, HVLP turbine, pumps, valves, and other electrical or electromechanical devices in the system 100. Suitable controllers can include a processor, a microprocessor, a control circuit, a PLC, or any other appropriate control device.

FIG. 11 also shows the controller 122 and the LCD user interface panel 107. The main controller 122 can be programmed many ways to operate the system 100 for its desired function. For example, in one embodiment, the controller has pre-programmed parameters such as fluid pump values (these control the speed of each fluid pump 113a-c via pulse width modulation which in turn controls how much fluid is applied over a period of time therefore controlling the intensity level of the fluid being sprayed), linear slide speed (this can control the speed of a linear slide that moves the nozzles 106a,b vertically up and down; this will also control the amount of solution applied over time and also the length of each application session), number of spray passes (this parameter controls how many times the body is sprayed). Any other variable that controls the operation of the machine can be stored and modified with the LCD interface display 107 and main controller 122.

With continued reference to FIG. 7, the LCD interface display 107 and main controller 122 can be programmed and configured to perform many unique application sessions. In one embodiment, a linear slide that moves nozzles 106a,b up and down vertically can be controlled with a motor drive system and any type of position encoding device. The encoding device can be connected to the main controller 122 so that the controller always knows the position of the nozzle arm 128a,b. This encoding system allows a user to select a partial body spray application. For example, the user can select to spray just their face, input their head height, and the system 100 will spray just their face with the desired solution or combination of solutions at the selected levels. Another example is that the user selects to just spray their legs or their whole body, excluding their legs or face or both. A height monitoring sensor can also be added to the control system so that it automatically adjusts the nozzle 106a,b positions for each user. This can also be used for full body sprays where the starting height of the nozzles 106a,b are adjusted to the height of each user, thereby reducing the amount of solution sprayed for bodies shorter than the maximum height of the nozzles 106a,b.

With reference back to FIGS. 1 and 2, the system 100 also includes a mist extraction column 103 a described above. The mist extraction column 103 can be mounted to the base 104 in a relative position opposite the spray column 102. The mist extraction column is used to capture any excess mist during spray sessions.

Figure 12:
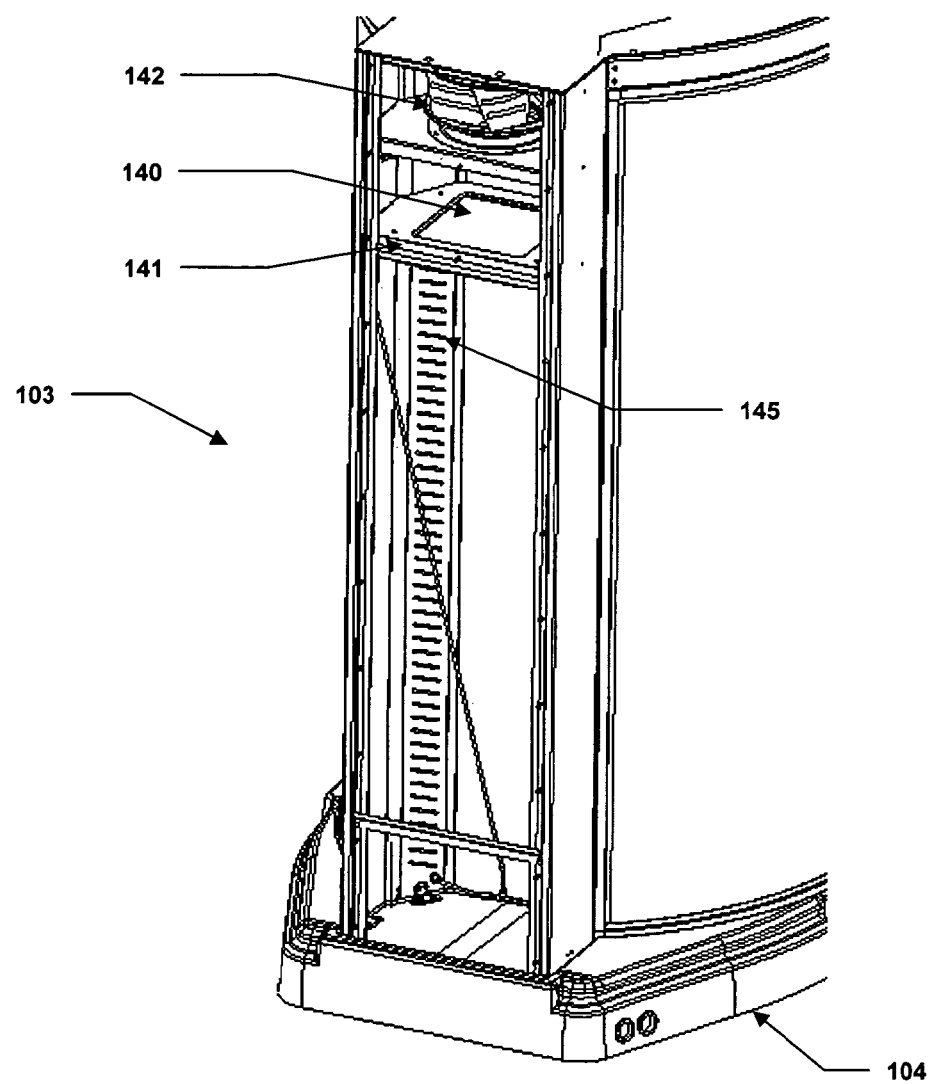
FIG. 12 is a perspective view showing the backside of the mist extraction column 103 with the rear cover removed.

FIG. 12 is a perspective view showing the internal components of the mist extraction column 103. The mist extraction fan 142 will be turned on by the controller 122 during a spray session to draw air flow and excess spray mist through vent openings 145 through a filter assembly 140 that is supported by a filter compartment 141. The mist is captured in the filter 141 and clean air is passed through the fan 142 and out the back of the mist extraction column 103. The size and CFM of the mist extraction fan 142 can be adjusted to provide the required amount of air flow to contain the mist generated by the HVLP nozzles 106a,b.

Figure 13:
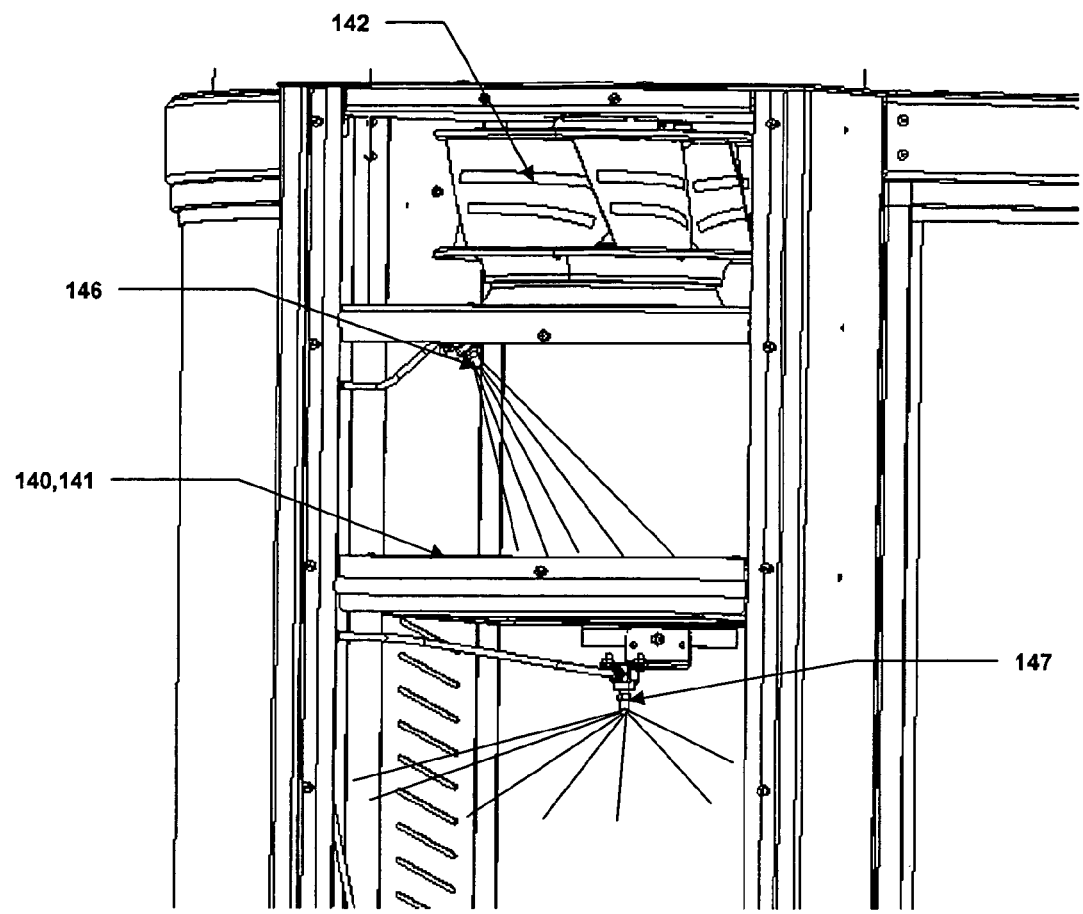
FIG. 13 is a perspective view showing a mist extraction fan 142, a mist extraction filter 140, a filter compartment 141, a filter wash down nozzle 146, and an internal column wash down nozzle 147 of the spray system 100.

FIG. 13 is a detailed perspective view of the internal components of the mist extraction column 103. Provided in a position relative to filter 140 is a filter wash down nozzle 146. The filter 140 in this embodiment is oriented in a horizontal position parallel to the ground plane.

The mist extraction column 103 also provides for an internal column wash down nozzle 147. This column wash down nozzle 147 can be used to clean the inside of the mist extraction column 103 to eliminate the buildup of any spray residue that may occur. This internal column wash down nozzle 147 can have a water supply line connected to it with a solenoid valve (not shown). This solenoid valve can be activated by the controller 122 to provide for a mist extraction column 103 cleansing cycle after each spray session or at desired intervals. In another embodiment, a manual valve could be used to control the water supply to the internal column wash down nozzle 147. The number of fans, filters, and nozzles or orientation of the fans, filters, and nozzles can be modified as needed.

Figure 14:
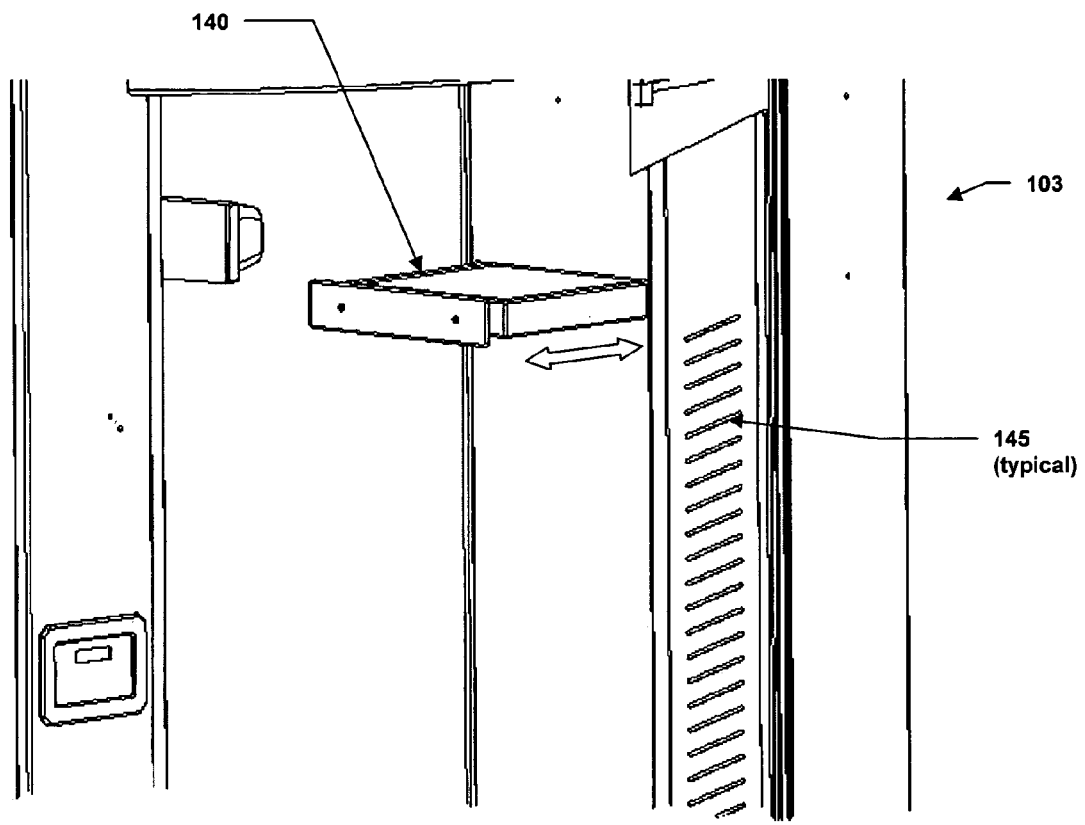
FIG. 14 is a perspective view showing the mist extraction filter 140 removed from the mist extraction column 103 and also showing the mist extraction column 103 inlet vents 145.

FIG. 14 shows how the filter is inserted and removed from the mist extraction column 103. The filter 140 slides in a direction perpendicular to the front of the mist extraction column 103 and allows for easy removal. The wash down nozzle 146 can have a water supply line connected to it with a solenoid valve (not shown). This solenoid valve can be activated by the controller 122 to provide for an automatic filter cleansing cycle after each spray session or at desired intervals. The horizontal position of the filter 140 in this embodiment allows for the filter cleansing water to be passed through the filter 140 and emptied at the bottom of the mist extraction column 103. In another embodiment, a manual valve could be used to control the water supply to the filter wash down nozzle 146.

Figure 15:
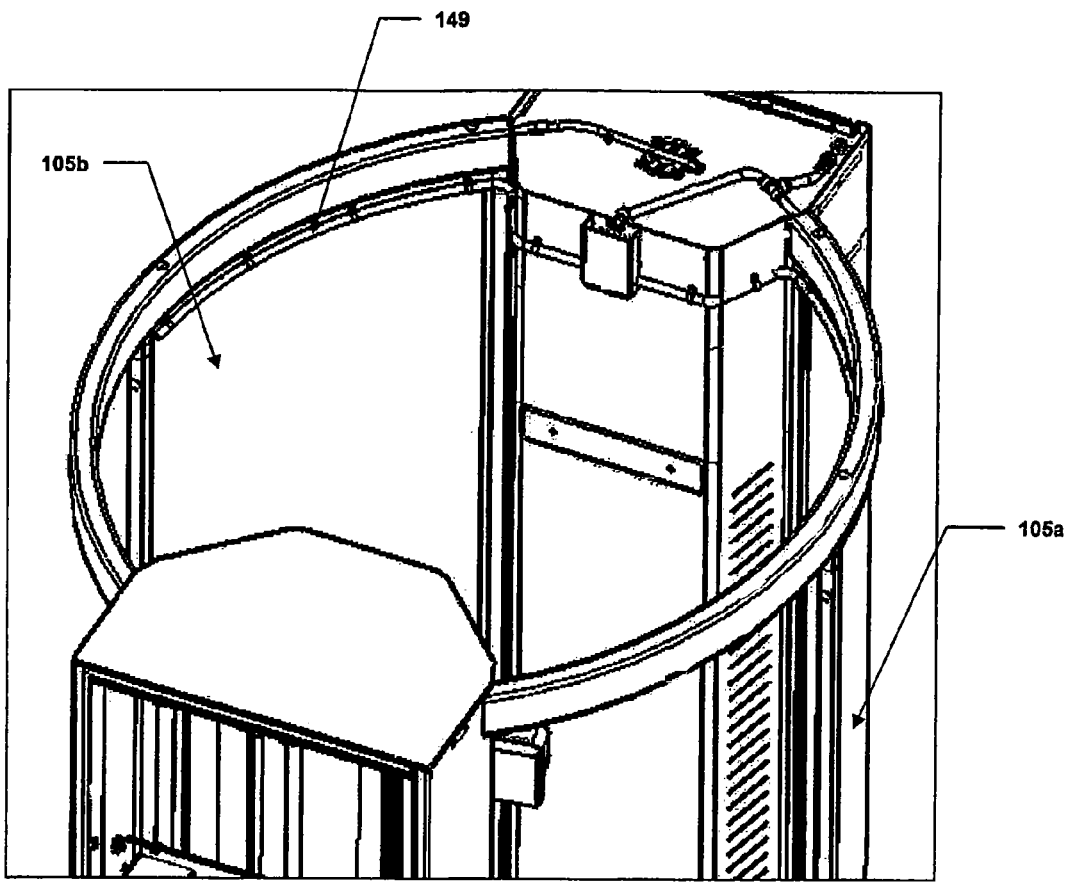
FIG. 15 is a perspective view showing one embodiment of a waterfall wash-down hose 149.

FIG. 15 shows a perspective view of a wash down system hose 149 used for this open system design. Because the system is open, care has to be taken when providing for an automatic wash down system so that excess wash down water does not leak out of the system. This embodiment shows the wash down hose 149 having holes along its length pointed toward its mounting surface. In this embodiment, the wash down hose 149 mounts along both side walls 105a,b and the mist extraction column 103. This configuration allows a waterfall-type wash down where the rinsing water is softly directed in a many small streams toward its relative mounting surface and runs down the surface to be cleaned. This waterfall wash down hose 149 can have a water supply line connected to it with a solenoid valve (not shown). This solenoid valve can be activated by the controller 122 to provide for system 100 cleansing cycle after each spray session or at desired intervals. In another embodiment, a manual valve could be used to control the water supply to the water fall wash down hose 149.

Figure 16:
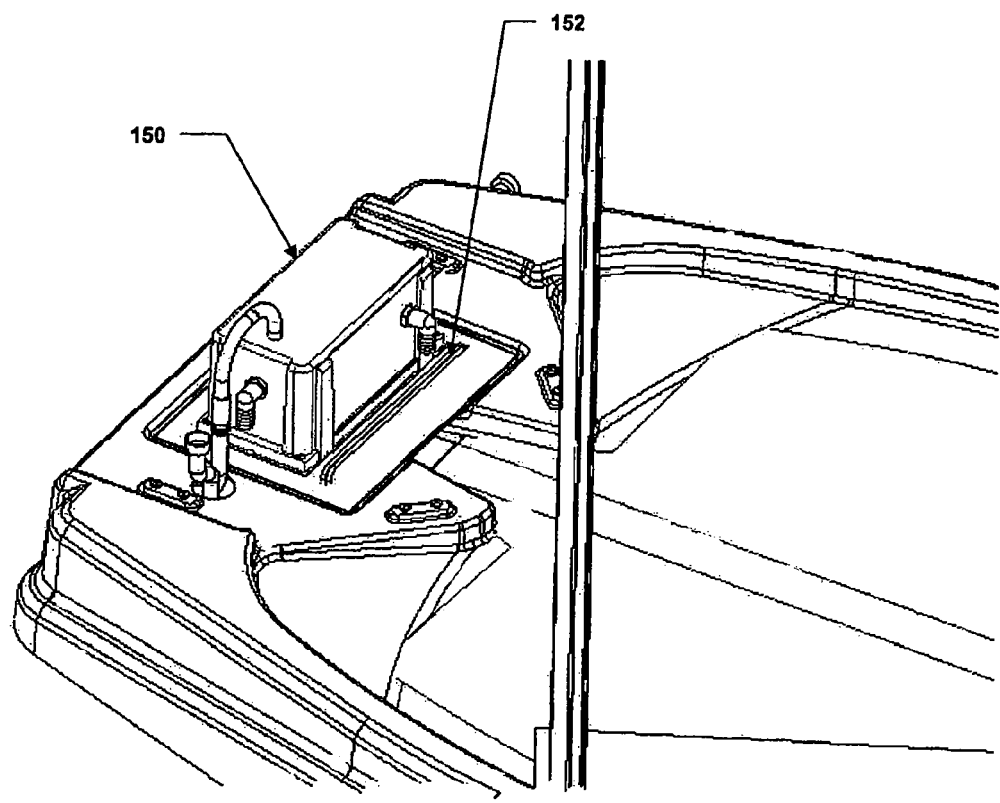
FIG. 16 is a perspective view showing one embodiment of a sump pump 150 waste water removal system and sump pump filter 152.
Figure 17:
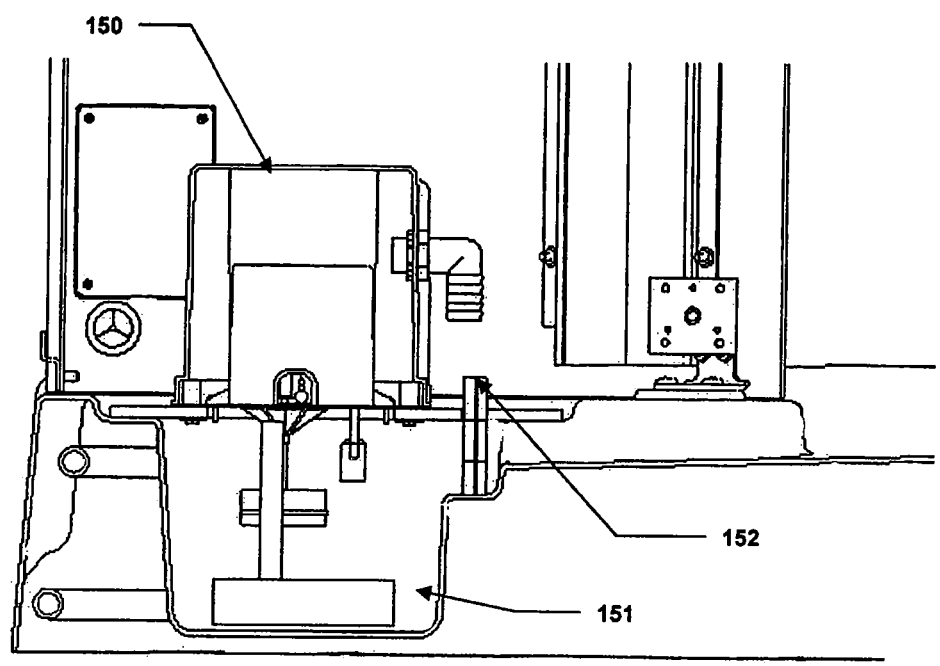
FIG. 17 is a side section view showing the sump pump 150 incorporated into a sump pump basin 151 that is integrated into the base 104 with a sump pump filter 152.

FIG. 16 shows a simplified perspective view of a waste water sump pump 150 mounted in base 104. FIG. 17 shows a side section view of a waste water sump pump 150 mounted in base 104. The base 104 has an integral drain basin 151 to catch waste water from the various wash down systems described above, including the filter wash down waste water, the internal column wash down waste water, and the system wash down waste water. The waste water from the above mentioned wash down systems flow down from their respective components to be cleaned over the top surface of the base 104 and towards the sump pump basin 151. The waste water also passes through a filter screen 152 to keep debris from entering the sump pump 150. The sump pump 150 will then pump out the waste water when its float switch activates the pump.

The fluid spraying system 100 can include additional components without departing from the scope of the present application. For example, the system 100 can include fluid detection sensors (not shown) disposed near the bottom of each fluid container 160a,b,c. The fluid detection sensors can be configured to sense the solution level in each fluid container 160a,b,c. When the solution level falls below a predetermined threshold, the fluid detection sensors can be configured to transmit a signal to the controller 122. Upon receipt of the signal, the controller 122 can deactivate the fluid spraying system 100 to prevent air from being pulled into one or all of the fluid flow paths F1, F2, and F3. Exemplary fluid detection sensors that can be employed include capacitive solution detection switches, optical sensors, or piezoelectric sensors.

Also, the fluid spraying system 100 can include a heating element (not shown), such as a heating coil or other heating device, that can be placed around or adjacent to the first and/or second and/or third fluid flow paths F1, F2, F3 thereby creating a warm, atomized mist of fluid that can be ejected from the nozzles 106a,b. Additionally, a heating element can be placed around or inside the air flow path A1. Alternatively, heating elements can be placed around or adjacent to one or all of the fluid containers 160a,b,c.

Figure 18:
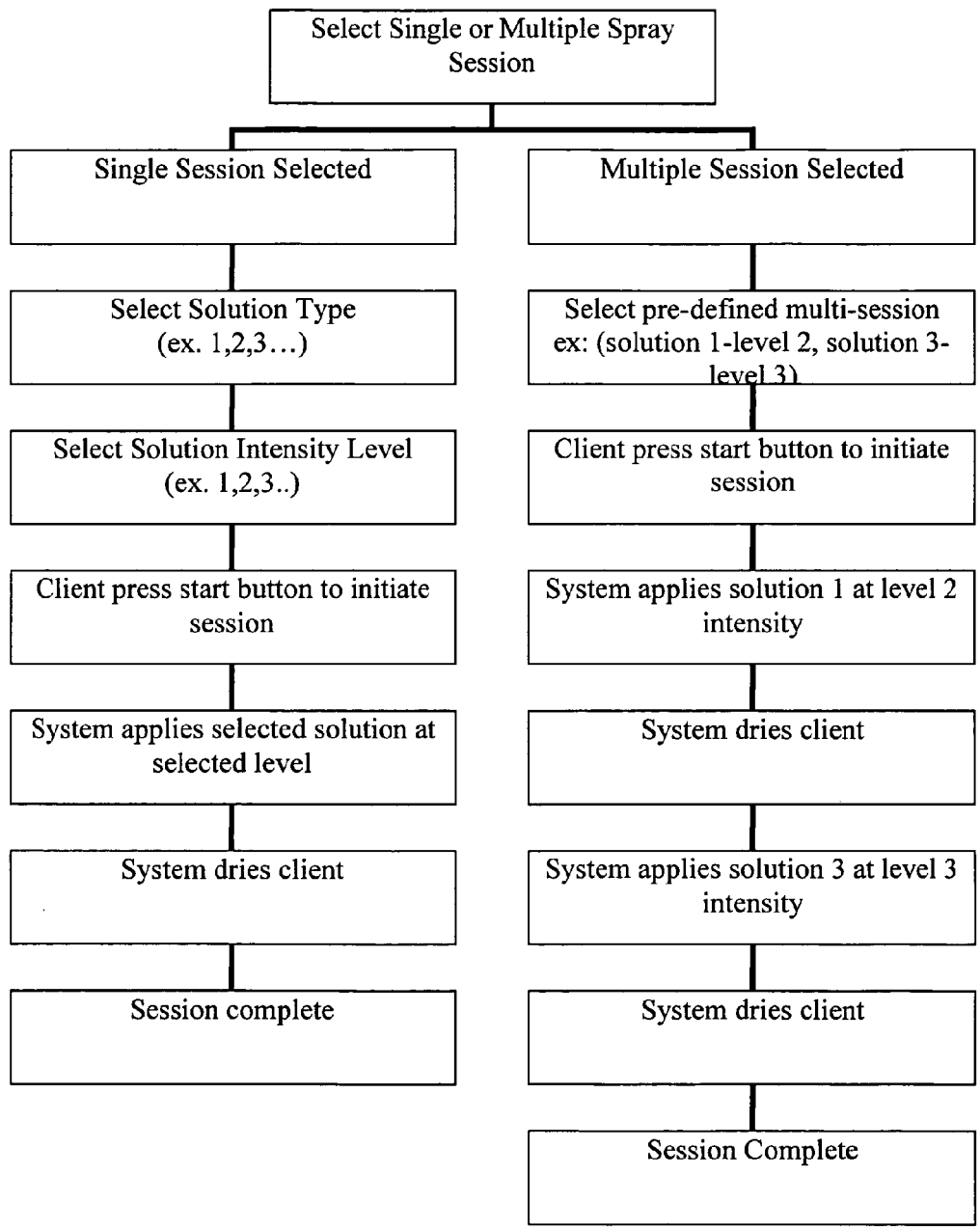
FIG. 18 is a flow chart illustrating one method for operating the automatic body spray system 100 to coat the human body that can be employed by a controller.

FIG. 18 is a flow chart showing one example of a control process. This process shown is for a full body session and a choice between a single solution spray or a multiple solution spray. The multiple solution spray shown in this example is for a two solution multispray but can be configured for any number of multi-session sprays. This flow chart can also apply for face only sprays, leg only sprays, or any other height adjustable spray session.

In one specific method to coat the human body, the method can include spraying can the atomized mixture of HVLP air and fluid onto the body and then turning off the fluid supply and moving the nozzles up and down with the HVLP air still on to dry the body. The speed, volume, and temperature natural to the HVLP air source is ideal for drying the body. Hence, the same nozzles that apply the atomized solution can also be used as a drying source when the solution is turned off and the air is turned on.

The system 100 described above and illustrated in the figures provides one or more of the following benefits: (1) the system does not require a large external air compressor for air delivery method, (2) the atomized spray using an HVLP air supply does not produce a lingering fog of mist and over spray, because of the lack of fog and over spray, (3) the system does not need to be completely enclosed to capture excess mist and keep it from escaping into the surrounding environment, (4) the user is not subjected to breath or be surrounded by excess fog or mist, and the transfer efficiency of the atomized fluid onto the human body is much higher than with compressed air systems, (5) the system allows many different types of products to be applied to the human body in one application session, (6) the system employs the use of a convenient slide out drawer to access the solution containers for multiple products to be applied, and (7) the system can be programmed to apply a fluid to only user specified areas of the body.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus, and illustrative examples shown and described. Accordingly, departures can be made from such details without departing from the spirit or scope of the applicant's general inventive concept. The system is not designed solely for sunless tanning products or for the purpose for spraying a human body. It can accommodate almost any type of product being sprayed.

What is claimed is:

1. An apparatus for extracting excess mist in a human body spray system, comprising:

a spray booth including:

a base configured to support the human body, a spray column, a mist extraction column disposed in an opposite position in the spray booth relative to the spray column, where the mist extraction column has a hollow interior and includes a substantially vertical first wall that forms at least a portion of an interior surface of the spray booth, the substantially vertical first wall having a plurality of vent openings disposed thereon, and a plurality of partial side walls disposed adjacent to the mist extraction column;

a filter disposed within the hollow interior of the mist extraction column; and an extraction fan disposed within the hollow interior of the mist extraction column; wherein the filter is disposed between the plurality of vent openings and the extraction fan; and wherein the extraction fan is configured to draw air flow and at least some of the excess mist through the plurality of vent openings and through the filter.

2. The apparatus of claim 1, further comprising:

a controller operably connected to the extraction fan and configured to control activation and deactivation of the extraction fan.

3. The apparatus of claim 1, where the filter is removably disposed within the hollow interior of the mist extraction column in a substantially horizontal orientation.

4. The apparatus of claim 1, further comprising:
   a column wash down nozzle disposed within the hollow interior of the mist extraction column and operably connected to a liquid supply and configured to spray liquid to cleanse a portion of an inside of the mist extraction column.

5. The apparatus of claim 4, where the liquid is water.

6. The apparatus of claim 4, further comprising a filter wash down nozzle disposed within the hollow interior of the mist extraction column above the filter and operably connected to the liquid supply, wherein the filter wash down nozzle is configured to spray liquid to cleanse the filter.

7. The apparatus of claim 6, wherein the filter is disposed substantially horizontally.

8. The apparatus of claim 4, further comprising:
   a solenoid valve operably connected to the liquid supply and the column wash down nozzle; and
   a controller operably connected to the solenoid valve to control activation and deactivation of the solenoid valve.

9. The apparatus of claim 8, where the controller is configured to automatically activate the solenoid after each spray session of the human body spray system to cause the column wash down nozzle to spray liquid in the direction of the portion of the inside of the mist extraction column.

10. The apparatus of claim 8, where the controller is configured to automatically activate the solenoid at intervals other than after each spray session of the human body spray system to cause the column wash down nozzle to spray liquid in the direction of the portion of the inside of the mist extraction column.

* * * * *